United States Patent
Kyrou et al.

(10) Patent No.: US 6,641,845 B1
(45) Date of Patent: Nov. 4, 2003

(54) SKIN WHITENING COMPOSITION COMPRISING BEARBERRY AND TETRAHYDROCURCUMIN

(75) Inventors: Christos D. Kyrou, Suffern, NY (US); Susan E. Simpson, Wyckoff, NJ (US); Dmitri Ptchelintsev, Mahwah, NJ (US); Dennis M. Martin, Cornwall, NY (US); Janice J. Teal, Old Greenwich, CT (US)

(73) Assignee: Avon Products, Inc., New York, NY (US)

( * ) Notice: Subject to any disclaimer, the term of this patent is extended or adjusted under 35 U.S.C. 154(b) by 183 days.

(21) Appl. No.: 09/587,129

(22) Filed: Jun. 2, 2000

Related U.S. Application Data

(63) Continuation of application No. 09/227,943, filed on Jan. 11, 1999, now abandoned, which is a continuation-in-part of application No. 09/109,107, filed on Jun. 30, 1998, now abandoned.
(60) Provisional application No. 60/083,528, filed on Apr. 29, 1998.

(51) Int. Cl.$^7$ ............................ A01N 65/00; A61K 35/78
(52) U.S. Cl. ..................... 424/725; 424/766; 424/777
(58) Field of Search ...................... 435/325; 424/195.1, 424/725, 766, 777

(56) References Cited

U.S. PATENT DOCUMENTS 6,174,533 B1 * 1/2001 SaNogueira, Jr. et al. .. 424/401

FOREIGN PATENT DOCUMENTS

JP          6-128133          5/1994

* cited by examiner

Primary Examiner—David M. Naff
Assistant Examiner—Deborah K. Ware
(74) Attorney, Agent, or Firm—Ohlandt, Greeley, Ruggiero & Perle LLP

(57) ABSTRACT

A preferred composition containing a skin whitening blend containing bearberry and an antioxidant, such as tetrahydrocurcumin, is provided. Also the composition can comprise a hypopigmenting component selected from mulberry, scutellaria, grape, cowberry, bilberry, molasses, pear, guava, licorice, etc. The licorice extract can be in the form of a water soluble extract or an oil soluble extract. Other antioxidants can be selected from rosemary extract, tocopherol, green tea extract, and gamma oryzanol. The skin whitening blend may also have an accelerant that enhances or accelerates the skin cell turnover rate. The skin whitening blend may also include a sunscreen component. Also, the composition may further include a pH adjusting agent, a surfactant, a thickening agent, a preservative, a fragrance, a masking agent, a pigment, an emulsifier, and/or emollient.

16 Claims, No Drawings

SKIN WHITENING COMPOSITION COMPRISING BEARBERRY AND TETRAHYDROCURCUMIN

RELATED APPLICATIONS

This is a continuation of application Ser. No. 09/227,943, filed on Jan. 11, 1999, now abandoned.

This application is a continuation-in-part of U.S. application Ser. No. 09/109,107, filed Jun. 30, 1998, now abandoned which is based on and claims priority in U.S. provisional application Ser. No. 60/083,528, filed on Apr. 29, 1998.

FIELD OF THE INVENTION

The present invention relates to a novel skin whitening blend that is a synergistic combination of a hypopigmenting component and an antioxidant. The skin whitening blend is further incorporated into a suitable topical vehicle to provide a skin whitening composition. Optionally, the novel skin whitening blend may also incorporate a sunscreen and/or a skin cell turnover rate accelerant.

OBJECTS OF THE INVENTION

It is an object of the present invention to provide an efficacious skin whitening blend that includes a hypopigmenting component and an antioxidant.

It is another object of the present invention to provide an efficacious skin whitening blend that further comprises a sunscreen and/or a skin cell turnover rate accelerant.

It is a further object of the present invention to provide an efficacious skin whitening composition that is the skin whitening blend of the present invention in a pharmaceutically elegant topical vehicle.

It is a still further object of the present invention to provide an efficacious skin whitening composition that is a cream.

It is yet a further object of the present invention to provide an efficacious skin whitening composition that is a lotion, solution, hydroalcoholic liquid, powder, pack or dermal patch.

DESCRIPTION OF THE PREFERRED EMBODIMENTS

The present invention relates to a skin whitening blend (hereinafter "skin whitening blend") that, is incorporated into a suitable topical vehicle to comprise the total skin whitening composition of the present invention. Unless otherwise defined, all percentages disclosed herein are weight percentages of the total skin whitening composition (hereinafter "composition").

Suitable topical vehicles for use in the present invention include cream, lotion, solution, hydroalcoholic liquid, pack, powder and dermal patch.

The activity/efficacy of the composition is defined herein as lightening of skin color, evening of skin tone/color, reduction in the appearance of solar lentigines (age spots) or ephilides (freckles), reduction of melasma, reduction of chloasma, reduction of post-inflammatory hyperpigmentation, reduction of pigmented keratoses, and/or the reduction of any sun-induced damage.

The first embodiment of the present invention is a composition having a skin whitening blend. The skin whitening blend has a hypopigmenting component and an antioxidant. In a second embodiment of the present invention, the skin whitening blend also has a component (hereinafter "accelerant") that enhances, or accelerates, the skin cell turnover rate. In a third embodiment of the present invention, the skin whitening blend has the hypopigmenting component, the antioxidant and a sunscreen, while a fourth embodiment has all three ingredients, plus the accelerant of the second embodiment.

The hypopigmenting component for all four embodiments includes one of the following constituents: (i) a licorice extract; (ii) a natural extract that includes at least one of the following extracts: hamamelitannin, mulberry, saxifraga, scutellaria, grape chlorella, bearberry, cowberry, bilberry, molasses, pear, guava, or a mixture thereof; and (iii) a blend of the licorice extract as defined in (i) and a natural extract blend as defined in (ii) (hereinafter "natural extract blend").

With regard to the natural extract (ii), any natural extract has hypopigmenting activity if used alone. However, to achieve the level of lightening of skin tone that is desired by applicants, it is preferred that the natural extract be a mixture of at least two extracts selected from the following group: hamamelitannin, mulberry, saxifraga, scutellaria, grape, chlorella, bearberry, cowberry, bilberry, molasses, pear and guava (hereinafter "natural extract mixture"). In a second preferred embodiment, the natural extract mixture has both pear and guava extracts. In a more preferred embodiment, the natural extract mixture has all of the following extracts: hamamelitannin, mulberry, saxifraga, scutellaria, grape, chlorella, bearberry, cowberry, bilberry, and molasses. In a most preferred embodiment, the natural extract mixture has all of the following extracts: hamamelitannin, mulberry, saxifraga, scutellaria, grape and bearberry. When the extract is either mulberry extract or scutellaria extract, it is preferred that at least a portion of the extract is derived from the root thereof.

When the hypopigmenting component has a licorice extract, either a water soluble (or aqueous) or an oil soluble licorice extract may be used.

Examples of suitable water soluble licorice extracts are glycolic licorice extracts, alcoholic licorice extracts, and combinations thereof. If a water soluble licorice extract is used, the concentration of the licorice extract is greater than about 0.001 wt % to about 30 wt %.

Ad An oil soluble licorice extract is the preferred licorice extract. Preferably, the oil soluble licorice extract is in powder form and is from about 0.001 wt % to about 5.0 wt %, more preferably from about 0.002 wt % to about 1.0 wt %, of the composition. It is even more preferable that the oil soluble licorice is from about 0.002 wt % to about 0.2 wt % of the composition. It is most preferable that the oil soluble composition is about 0.05.wt % to about 0.1 wt % of the composition. The oil soluble licorice extract may have one or more of the following constituents: glabridin, glabrene, formononetin, glabrol and other related phenolic compounds. Examples of phenolic compounds may include hispaglabridin-A, 4'-O-methylglabridin, and 3' hydroxy-4' O-methylglabridin.

It is preferred that the hypopigmenting component is the licorice extract (i). The more preferred hypopigmenting component for the composition is the natural extract blend (iii), (which includes both the licorice extract (i) and the natural extract (ii)). However, it is even more preferred that the hypqpigmenting component is the combination of the more preferred embodiment of the licorice extract (i) and the more preferred first embodiment of the natural extract mixture (ii). It is most preferred that the hypopigmenting component is the combination of the most preferred embodiment of licorice extract (i) and the most preferred first embodiment of the natural extract mixture (ii).

If the hypopigmenting component is the mixture of natural extracts as defined by (ii), the natural extract mixture may have from about 0.1 wt % to about 99.0 wt % of a mixture that has at. least two of the following extracts: hamamelitannin (*Hamamelis virginiana*), mulberry, saxifraga, scutellaria, grape, *Chlorella vulgaris*, bearberry (*Arctostaphylos uva ursi*), cowberry (*Vaccinium vitis idaea*), bilberry (*Vaccinium myrtillus*), or molasses (Black Sugar).

A second example of the natural extract mixture has from about 0.1 wt % to about 99 wt % of hamamelitannin extract and from about 0.01 wt % to about 99 wt % of each of the following extracts: mulberry, saxifraga, scutellaria, grape, and bearberry. More preferably, the second example of the natural extract mixture is from about 5 wt % to about 30 wt % hamamelitannin extract, from about 0.1 wt % to about 10 wt % of each of the following extracts: mulberry, saxifraga, scutellaria, grape, and bearberry.

A third example of the natural extract mixture has from about 0.1 wt % to about 99 wt % of hamamelitannin extract and from about 0.01 wt % to about 99 wt % of each of the following extracts: mulberry, saxifraga, scutellaria, grape, chlorella, bearberry, cowberry, bilberry, and molasses. More preferably, the third example of the natural extract mixture is from about 5 wt % to about 30 wt % hamamelitannin extract, and from about 0.1 wt % to about 10 wt % of each of the following extracts: mulberry, saxifraga, scutellaria, grape, chlorella, bearberry, cowberry, bilberry, and molasses.

A fourth example of the natural extract mixture has about 0.01 wt % to about 99 wt %,pear extract, and from about 0.01 wt % to about 99 wt % guava extract. More preferably, the fourth example of the natural extract mixture has from about 0.1 wt % to about 10 wt % pear extract, and from about 0.1 wt % to about 10 wt % guava extract.

The second component in all four embodiments of the present invention is an antioxidant. The antioxidant may comprise the following extracts: green tea, *Rosemarinus officinalis* (hereinafter "rosemary"), gamma oryzanol, a tocopherol or tocopherol derivative, tetrahydrocurcumin or mixtures thereof. Although any one of the aforementioned antioxidants will exhibit activity when used individually, it is preferred that the antioxidant is at least two of the antioxidant extracts. It is most preferred that the antioxidant is a mixture of all four antioxidants. The total amount of antioxidant in the composition is from about 0.0001 wt % to about 50 wt %.

The green tea extract may be aqueous, alcoholic, glycolic, oil miscible powder, or a combination thereof. If the green tea extract is aqueous, alcoholic, or glycolic, then the green tea extract is from about 0.0001 wt % to about 30 wt % of the composition.

It is preferable that the green tea extract is a green tea extract powder in which the minimum of polyphenol content is about 65 wt % of the green tea extract powder, and that the polyphenol content comprises epicatechin gallate (ECG) and epigallocatechin gallate (EGCG). However, other additional ingredients can be included in the polyphenol content. When a green tea extract powder with the polyphenol content as defined above is used, the composition is from about 0.0001 wt % to about 5.0 wt % of the green tea extract powder and, more preferably, from about 0.0001 wt % to about 1.0 wt % of the green tea extract powder.

The rosemary extract may also be aqueous, alcoholic, glycolic, oil miscible powder, or a combination thereof. The rosemary extract is from about 0.001 wt % to about 30 wt %. It is more preferable that an oil miscible rosemary extract is from about 92 wt % to about 98 wt % dry powder. When such an oil miscible rosemary extract powder is used, the composition is from about 0.001 wt % to about 15 wt % of the rosemary extract powder, and, more preferably, from about 0.05 wt % to about 5 wt % of the rosemary extract powder.

The antioxidant may also have from about 0.001 wt % to about 15 wt %, preferably from about 0.01 wt % to about 5 wt %, gamma oryzanol. The antioxidant component further includes from about 0.01 wt % to about 10 wt %, preferably about 0.1 wt % to about 5 wt %, of a tocopherol or tocopherol derivative. Examples of suitable tocopherol derivatives are vitamin E acetate, vitamin E nicotinate and vitamin E linoleate.

A preferred antioxidant is tetrahydrocurcumin. In a preferred embodiment, tetrahydrocurcumin is present in an amount about 0.001 wt % to about 20 wt %. In a more preferred embodiment, tetrahydrocurcumin is present in an amount about 0.1 wt % to about 10 wt %, and most preferably is present in an amount about 0.5 wt % to about 5 wt %. It is more preferred that the antioxidant of the present invention includes tetrahydrocurcemin.

It has been found that a skin whitening compositions of the present invention having both tetrahydrocurcumin and a hypopigmenting blend of natural extracts demonstrate an unexpected, synergistic whitening/depigmenting activity as compared to either tetrahydrocurcumin or a hypopigmenting blend of natural extracts individually.

An in vivo comparative test of three skin whitening compositions was conducted measuring the development of pigmentation on skin after exposure to irradation of 1 MED (Minimum Erythemal Dose). The active components of Samples A, B and C are set forth below.

SAMPLE A 3,6,9-Trioxaundecanedioic Acid
Vitamin E Acetate
Gamma Oryzanol
Rosemary Extract Powder
Licorice Extract (oil soluble powder)
Green Tea Extract Powder
Mulberry Extract Powder
Uva Ursi Extract
Hamamelitannin Extract
Saxifraga Extract
Grape Extract
Mulberry Root Extract
Scutellaria Root Extract

SAMPLE B 3,6,9-Trioxaundecanedioic Acid
Vitamin E Acetate
Gamma Oryzanol
Rosemary Extract Powder
Licorice Extract (oil soluble powder)
Green Tea Extract Powder
Mulberry Extract Powder
Uva Ursi Extract
Saxifraga Extract Grape Extract
Mulberry Root Extract
Scutellaria Root Extract
Tetrahydrocurcumin

SAMPLE C

Tetrahydrocurcumin j

Control

Untreated Skin

An area of human skin was treated with either sample A, B or C and then exposed to irradiation equivalent to 1 MED (Minimum Erythemal Dose). The test areas were observed over a period of eight days, with the observations occurring daily from days 4 through 8. The results of the tests are set forth below in Table 1.

TABLE 1

|  | Degree of Pigmentation |
|---|---|
| CONTROL | 0.5 |
| SAMPLE A | 0.2 |
| SAMPLE B | 0.1 |
| SAMPLE C | 0.3 |

As demonstrated by the results set forth in Table 1, the presence of tetrahydrocurcumin in a skin whitening composition of the present invention produces an unexpected synergistic skin whitening effect as compared to a skin whitening compositions without tetrahydrocurcumin or a tetrahydrocurcumin alone.

In the second embodiment of the present invention, the skin whitening blend further comprises an accelerant. The accelerant aids in increasing the skin cell turnover rate, and thereby augments the skin whitening activity of the first embodiment of the present invention.

Examples of suitable accelerants are oxa acids, oxa diacids (hereinafter also referred to as "oxa acids"), retinoids and retinoid derivatives, which are preferably retinol and retinol derivatives. Preferably, the composition has from about 0.001 wt % to about 10 wt % accelerant. If the accelerant is retinol or a retinol derivative, the composition has from about 0.001 wt % to about 5 wt % retinol or the retinol derivative. If the accelerant is a retinoid or retinoid derivative, then it is preferable that the retinoid is retinol or a retinol derivative. If the accelerant is an oxa acid or a combination of oxa acids, the composition preferably has from about 0.5 wt % to about 10 wt % oxa acid. Oxa acids suitable for use in the present invention are disclosed in co-pending U.S. patent applications Ser. No. 08/636,540 and 08/658,089. The entire disclosures of each of the aforementioned patent applications are herein incorporated by reference. If an oxa acid accelerant is used, then preferably the composition has from about 0.5 wt % to about 10 wt % of 3-6-9-trioxaundecanedioic acid. In addition, if the accelerant is an oxa acid or a combination of oxa acids, then the pH of the composition is optimally about 3.5 to about 4.5.

The third embodiment of the skin whitening blend has the hypopigmenting component, the antioxidant, and further comprises, a sunscreen. The sunscreen may be any sunscreen or any combination of two or more sunscreens, known in the art to be suitable for use in a topical composition. The sunscreen is from about 0.001 wt % to about 40 wt %, and more preferably from about 3 wt % to about 25 wt % of the composition.

Examples of suitable sunscreens and suitable concentrations thereof are as follows: from about 0.001 wt % to about 10 wt % ethylhexyl p-methoxy cinnamate (non-limiting examples of suitable ethylhexyl p-methoxy cinnamates are those available from the Givaudan Corporation under the tradename "Parsol MCX", from Van Dyk Incorporation under the tradename "Escalol 557", from Haarman & Reimer Corporation under the tradename "Neo Heliopan Av", and from BASF under the tradename "Uvinul MC80"), from about 0.001 wt % to about 10 wt % oxybenzone or benzophenone-3 (non-limiting examples of suitable oxybenzones are those available from ISP Van Dyk under the tradename "Escalol 567", from BASF under the tradename "Uvinul M40", from Neville Synthese Chem. Co./Rhone Poulenc (Rhodia, Inc.) under the tradename "Syntase 62", and from Rona/EM Ind. under the tradename "Eusolex 4360" product #605376), from about 0.001 wt % to about 10 wt % sulisobenzone, from about 0.001 wt % to about 3.0 wt % dioxybenzone, from about 0.001 wt % to about 5 wt % of menthyl anthranilate, from about 0.001 wt % to about 25 wt % titanium dioxide, from about 0.001 wt % to about 20 wt % of zinc oxide, from about 0.001 wt % to about 10 wt % of a flavonoid or a derivative thereof, from about 0.001 to about 10 wt % butyl methoxydibenzoylmethane (a non-limiting example of a suitable butyl methoxydibenzoylmethane is available from Roche Inc. under the trade name "Parsol-1789" product #64030), from about 0.001 wt % to about 10 wt % 4-isopropyldibenzoyl-methane, from about 0.001 wt % to about 10 wt % octyl triazone, and from about 0.001 wt % to about 25 wt % of a sunscreen of titanium dioxide, zinc oxide and methicone that is manufactured by Miyoshi Kasei and distributed by U.S. Cosmetics under the tradename "TZ Powder type I(B)."

One preferred sunscreen includes about 7.5 wt % ethylhexylmethoxycinnamate, about 2 wt % butyl methoxydibenzoylmethane and from about 3 wt % to about 4 wt % oxybenzone/benzophenone-3.

In the fourth, most preferred, embodiment of the present invention, the skin whitening blend has the hypopigmenting component, the antioxidant, the accelerant and the sunscreen. For the fourth embodiment, the parameters of each component are the same as set forth above. The fourth embodiment is most preferred because the skin whitening effects of the first embodiment are enhanced by the increased skin cell turnover rate accomplished by the accelerant, and the addition of the sunscreen functions to protect consumers from the damaging effects of ultraviolet radiation.

The compositions of the present invention can have one or more other ingredients such as, for example, an alcohol, a pH adjusting agent, chelating agent, emollient, emulsifier, film former, humectant, fragrance, masking agent, pigment, preservative, powder, surfactant, and thickening agent.

The pH adjusting agent is preferably a base. The preferred bases are ammonium hydroxide, potassium hydroxide and sodium hydroxide. Potassium hydroxide and ammonium hydroxide are more preferred. Theoretically, other pH adjusting agents may be suitable for use in the present invention, if the pH adjusting agent both provides a stable composition and adjusts the pH of the composition to a pH that suitable for topical use. As stated above, when the accelerant is an oxa acid, the pH of the composition is optimally from about 3.5 to about 4.5.

The preferred compositions of the present invention may have the following:

EXAMPLE 1

| INGREDIENT | PERCENTAGE |
| --- | --- |
| 3,6,9-Trioxaundecanedioic Acid | 0.001–10.0 |
| Ammonium Hydroxide | 0.001–4.0 |
| Humectants (e.g. Glycols, Glycerols) | 0.5–15.0 |
| Thickeners (e.g. Gums, Starches, Polymers) | 0.1–4.0 |
| Chelants | 0.001–0.5 |
| Emollients | 1.0–10.0 |
| Silicones | 0.1–15.0 |
| Preservatives | 0.01–2.0 |
| Fatty Alcohols/Emulsifiers/Waxes/Fatty Acids | 0.5–15.0 |
| Alcohols | 0–10.0 |
| Vitamin E Acetate | 1.0 |
| Gamma Oryzanol | 0.5 |
| Extracts | 12.35 |
| Ethylhexylmethoxycinnamate | 7.5 |
| Butyl Methoxy Dibenzoylmethane | 2.0 |
| Benzophenone–3 | 3.5 |
| Demineralized Water | Q.S. |

The following is a composition of the present invention that has been tested in vitro and found to provide the desired efficacious skin whitening composition.

EXAMPLE 2

| INGREDIENTS | PERCENTAGE |
| --- | --- |
| 3,6,9-Trioxaundecanedioic Acid | 0.001–10.0 |
| Ammonium Hydroxide | 0.001–4.0 |
| Humectants (e.g. Glycols, Glycerols) | 0.5–15.0 |
| Thickeners (e.g. Gums, Starches, Polymers) | 0.1–4.0 |
| Chelants | 0.001–0.5 |
| Emollients | 1.0–10.0 |
| Silicones | 0.1–15.0 |
| Preservatives | 0.01–2.0 |
| Fatty Alcohols/Emulsifiers/Waxes/Fatty Acids | 0.5–15.0 |
| Alcohols | 0–10.0 |
| Vitamin E Acetate | 1.0 |
| Gamma Oryzanol | 0.5 |
| Rosemary Extract Powder | 0.2 |
| Licorice Extract (oil soluble powder) | 0.05 |
| Green Tea Extract Powder | 0.0004 |
| Mulberry Extract Powder | 0.1 |
| Uva Ursi Extract | 1.0 |
| Tetrahydrocurcumin | 1.0 |
| Blend of Saxifraga, Grape, Mulberry Root, and Scutellaria Root Extracts | 1.0 |
| Ethylhexylmethoxycinnamate | 7.5 |
| Butyl Methoxy Dibenzoylmethane | 2.0 |
| Benzophenone-3 | 3.5 |
| Demineralized Water | Q.S. |

Various modifications and alterations to the present invention may be appreciated based on a review of this application. These changes and additions are intended to be within the scope and the spirit of the present invention as defined by the following claims.

We claim:

1. A composition for whitening comprising:
   A. about 0.1 wt % to about 99 wt % bearberry extract; and
   B. about 0.0001 wt % to about 50 wt % tetrahydrocurcumin.

2. The composition of claim 1, further comprising an accelerant that enhances skin cell turnover rate.

3. The composition of claim 2, wherein the accelerant is selected from the group consisting of an oxa acid, a combination of oxa acids, retinoids, retinoid derivatives, and mixtures thereof.

4. The composition of claim 3, wherein the accelerant is from about 0.001 wt % to about 10 wt % of the composition.

5. The composition of claim 2, further comprising a pH adjusting agent, wherein the pH adjusting agent is selected from the group consisting of ammonium hydroxide, potassium hydroxide and sodium hydroxide.

6. The composition of claim 1, further comprising a sunscreen.

7. The composition of claim 6, wherein the sunscreen is from about 0.001 wt % to about 40 wt % of the composition.

8. The composition of claim 1, further comprising a licorice extract, wherein the licorice extract is selected from the group consisting of a water soluble licorice extract and an oil soluble licorice extract.

9. The composition of claim 8, wherein the licorice extract is a water soluble licorice extract in an amount from about 0.001 wt % to about 30 wt % of the composition, wherein the licorice extract is an oil soluble licorice extract in an amount from about 0.001 wt % to about 5.0 wt % of the composition.

10. The composition of claim 8, wherein the oil soluble extract is in a powder form and is present in an amount from about 0.002 wt % to about 1.0 wt % of the composition.

11. The composition of claim 1, further comprising an ingredient selected from the group consisting of green tea extract, rosemary extract, gamma oryzanol, a tocopherol or tocopherol derivative, and mixtures thereof.

12. The composition of claim 1, further comprising an ingredient selected from the group consisting of a film former, a pigment, and a preservative.

13. A method of whitening skin comprising topically applying the composition of claim 1 to the skin.

14. A composition for whitening skin comprising:
   A. about 0.1 wt % to about 99 wt % bearberry extract; and
   B. about 0.0001 wt % to about 50 wt % tetrahydrocurcumin, wherein the composition is a topical composition.

15. A method of whitening skin comprising topically applying the composition of claim 14 to the skin.

16. A method of enhancing the hypopigmenting activity of a skin whitening composition comprising about 0.1 wt % to about 99 wt % bearberry extract as a hypopigmenting component, comprising adding tetrahydrocurcumin to the composition in an amount of about 0.0001 wt % to about 50 wt % effective to synergistically enhance hypopigmenting activity of the hypopigmenting component.

* * * * *